United States Patent

Hubbe

[19]

[11] Patent Number: 5,936,151
[45] Date of Patent: Aug. 10, 1999

[54] METHOD AND APPARATUS FOR MEASURING AN ELECTRICAL PROPERTY OF PAPERMAKING FURNISH

[75] Inventor: Martin Allen Hubbe, Campbell Hall, N.Y.

[73] Assignee: International Paper Company, Purchase, N.Y.

[21] Appl. No.: 08/995,672

[22] Filed: Dec. 22, 1997

[51] Int. Cl.[6] .................................................. G01N 33/34
[52] U.S. Cl. ............................................................ 73/53.03
[58] Field of Search ................................ 73/53.03, 64.56, 73/864.35, 863.84; 162/49, 198, 263

[56] References Cited

U.S. PATENT DOCUMENTS

| | | | |
|---|---|---|---|
| 3,654,551 | 4/1972 | Flinchbaugh | 324/71 CP |
| 4,517,285 | 5/1985 | Woodward et al. | 430/538 |
| 4,535,285 | 8/1985 | Evans et al. | 324/71.1 |
| 4,752,356 | 6/1988 | Taggert et al. | 162/198 |
| 4,873,489 | 10/1989 | Melcher et al. | 324/453 |
| 4,891,098 | 1/1990 | Renjilian et al. | 73/53.03 |
| 4,961,147 | 10/1990 | Moore | 324/71.1 |
| 5,119,029 | 6/1992 | Bryant et al. | 324/453 |
| 5,202,016 | 4/1993 | Church et al. | 210/85 |
| 5,220,283 | 6/1993 | Dentel | 324/453 |
| 5,365,775 | 11/1994 | Penniman | 73/53.03 |
| 5,373,229 | 12/1994 | Penniman | 324/71.1 |
| 5,408,185 | 4/1995 | Krah | 324/453 |
| 5,495,751 | 3/1996 | Petzold et al. | 73/53.03 |

*Primary Examiner*—Robert Raevis
*Attorney, Agent, or Firm*—Luedeka, Neely & Graham, P.C.

[57] ABSTRACT

An apparatus for determining an electrical characteristic of a papermaking furnish includes a sample chamber having first and second sections for containing a sample of the papermaking furnish. A fiber-collecting screen having a mesh sufficient to inhibit the passage of suspended fibers separates the first and second sections of the sample chamber. Furnish is urged back and forth through the screen in a plurality of cycles so that as furnish flows in one direction through the screen, a fiber pad is formed adjacent the screen and as furnish is moved through the screen in a second direction, the fiber pad is expelled from the screen back and redispersed back into the furnish sample. A stirrer or mixer assists in removing the fiber pad from the screen and in redispersing fibers comprising the fiber pad back into the furnish sample. As furnish is urged through the screen, electrodes positioned on opposite sides of the screen produce signal outputs corresponding to an electrical characteristic of the furnish. A voltmeter receives the electrode outputs and measures voltage across the screen. In one embodiment, furnish is moved through the screen by means of a variable volume chamber in fluid connection with the screen and furnish. In an alternate embodiment, fluid is urged through the screen by reciprocating the screen within the furnish sample. Colloidal charge of the furnish may be determined by moving furnish through the screen in repeated cycles as the furnish sample is titrated with a highly charged additive.

29 Claims, 7 Drawing Sheets

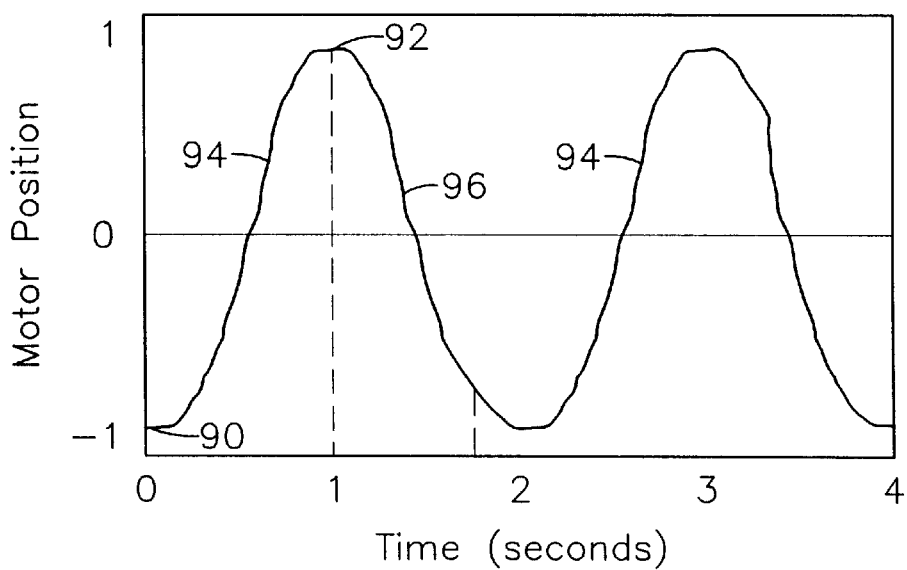
*Fig.*7A
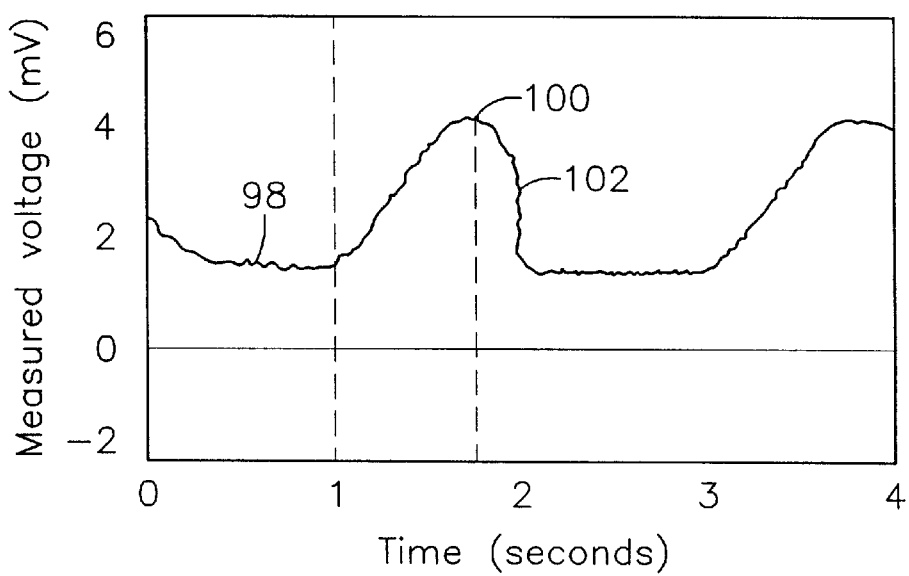
*Fig.*7B

METHOD AND APPARATUS FOR MEASURING AN ELECTRICAL PROPERTY OF PAPERMAKING FURNISH

TECHNICAL FIELD

The present invention relates generally to devices for measuring electrokinetic properties of an aqueous dispersion or suspension, and particularly to an apparatus which measures the streaming potential of papermaking furnish.

BACKGROUND

During papermaking operations, an aqueous slurry of cellulosic fibers known as "furnish" is dewatered on a moving screen or "wire" (sometimes referred to as a forming fabric). Fibers and other particulates become trapped on the wire, forming a fibrous web which is further processed into the end product. Depending on the grade of paper being produced, the furnish may also contain suspended solids such as mineral fillers and emulsified additives along with various soluble materials to improve and/or modify the paper properties.

Examples of such suspended solids include clay, calcium carbonate, titanium dioxide, dyes and rosin. To achieve the desired paper properties of various paper and paperboard grades, it is essential that these ingredients be retained efficiently during the forming of the paper web and not flow through the wire with the water draining from the web. Papermakers employ combinations of various additives, including very high mass acrylamide copolymers (retention aids), highly cationic polymers (promoters), and anionic colloidal particles or polymers (microparticles) to promote retention of these suspended solids.

The furnish used by most papermakers is composed mainly of cellulosic fibers such as groundwood pulp, chemithermomechanical pulp (CTMP), kraft pulp, or sulfite pulp.

It is the nature of these pulp varieties that they have, at the fiber surfaces, a negative (anionic) colloidal charge. Other pulp varieties or samples of furnish selected from some papermaking processes, however, may exhibit positive (cationic) colloidal charges.

Variations in the electrokinetic properties of the furnish, including the colloidal charge of the furnish, can have a profound effect on retention, drainage during web formation, and paper properties. For example, if a new batch of pulp contains a higher level of dissolved anionic polymers and colloidal anionic material (disco), then the percentage of fine material retained during a single pass over the forming fabric (first-pass retention) may be decreased. Variations in parameters such as retention and drainage can also have an immediate effect on the tension control of the machine, which effects dimensional stability and can lead to web breaks and attendant downtime as well as nonuniform web properties. Therefore, stability in the colloidal charge is a critical papermaking furnish characteristic since it can significantly affect the quality, uniformity and rate of production in papermaking.

Prior attempts to monitor and control the electrokinetic properties of papermaking furnish have included laboratory-based tests where a sample is withdrawn from the furnish or from the whitewater which drains from the furnish during web formation. Some on-line systems have also been attempted.

Lab-scale tests include micro-electrophoresis, in which a microscope is used to observe the motion of a particle in a capillary cell while under the influence of an imposed electric field. The quotient of the particle velocity and the field strength defines the particle's electrophoretic mobility. When the viscosity of the fluid and its conductivity are known, this method is used to calculate the "zeta potential", which is the electrical potential at the hydrodynamic slip plane at the surface of the particle. As a particle moves through the fluid, a double layer of charge is built up—a layer at the surface of the particle and another layer produced by diffuse ions that remain close to the particle's surface during motion. Zeta potential, which is the electrical potential created by both layers of charge, is frequently used by papermakers as an indication of the state of electrokinetic charge in the system.

In order for micro-electrophoresis to work, the particles must be much smaller than the diameter of the capillary cell in which the tests are conducted. This poses a significant limitation in furnish analysis due to the relatively large size of cellulose fibers used in papermaking. In many cases, this size limitation requires screening the papermaking furnish and testing only the fine suspended solids remaining in the filtrate, or white-water. The capillaries used are also subject to contamination by particulates within the furnish.

Moreover, focusing a microscope tends to be too delicate of an operation for practical application in the industrial environment of a paper mill. If the microscope is incorrectly focused, this can cause incorrect readings. In addition, the information obtained about the electrophoretic mobility of a particle is usually not linearly proportional with any process or additive which is under the direct control of papermakers.

Another approach has been to employ a streaming current apparatus to measure another electrokinetic effect related to the charged properties of polymers, colloids, and fine particles in the sample. A streaming current device typically employs a plunger or piston which is reciprocated within a polytetrafluoroethylene (PTFE, commonly referred to as Teflon™) cylinder closed at one end. The diameter of the piston is slightly smaller than the diameter of the PTFE cylinder so that the reciprocating motion of the piston causes fluid to move rapidly in the narrow annular space between the piston and cylinder wall. The motion of the fluid through this space in the direction parallel to the cylinder movement induces a streaming current resulting from colloidal materials adsorbing onto the PTFE cylinder wall, which is detectable by appropriate connection of an ammeter or voltmeter to the cylinder wall. In use of a streaming current device, the papermaker may titrate a known volume of whitewater or furnish with a highly charged (cationic) polymer, such as poly-diallyldimethylammonium chloride (DADMAC), or other material. The titration is continued until the streaming current apparatus indicates a zero signal. The amount of titrant added is used to calculate the net charge of the sample. A significant disadvantage of the streaming current method, however, is that the method is significantly affected by materials such as sodium sulfate and potassium chloride which are commonly present in papermaking samples. Such materials tend to increase the conductivity of the sample and significantly reduce the ability to accurately measure electrokinetic properties of the furnish. Also, such devices do not exhibit equivalent utility for different types of furnish. For example, streaming current devices have been observed to perform poorly when carrying out a charge titration experiment with alkaline and de-inked pulps.

A further approach to determining the electrokinetic properties of fiber furnish is called streaming potential. This approach measures the potential resulting from fluid flow through a pad of fibers. As furnish flows through the pad, diffuse ions in the outer layer of charge are removed, allowing estimation of the zeta potential at the fiber surfaces. This potential is measured by placing electrodes adjacent the pad. The measurements are repeated often enough to give the papermaker "a good idea" of how the zeta potential at the fiber surface varies as a function of time.

Prior art streaming potential devices suffer from various disadvantages which tend to produce unreliable data. For example, the absolute magnitudes of the zeta potential determined from known streaming potential devices depends on the extent of compaction of the fiber pad, which is difficult to control. Furthermore, in order to obtain an accurate measure of the zeta potential of a sample it is necessary to repeat the experiment several times at different densities of the fiber mat and extrapolate to zero solids. Spurious results are often observed when measuring high conductivity pulps. Another difficulty is that the electrodes of prior art streaming potential devices tend to drift, producing inaccuracies in the measurements. Additionally, streaming potential measurement devices do not provide the papermaker with information about colloidal charge.

Therefore, it is an object of the present invention to provide a method and apparatus for determining an electrokinetic property of a papermaking furnish in order to provide reliable formation-related data to papermakers.

Another object of the present invention is to provide a method and apparatus for quantifying the colloidal charge of a papermaking furnish.

A further object of the present invention is to provide a method and apparatus for accurately and efficiently determining the algebraic sign and relative magnitude of streaming potential of a papermaking furnish to obtain superior control of charge balance within the furnish.

Yet another object of the present invention is to provide a method and apparatus of the character described which promotes efficient use of fiber furnish additives such as highly charged cationic polymers.

An additional object of the present invention is to provide an automated method and apparatus for determining an electrokinetic property of a papermaking furnish, and from that determination, adjusting furnish additives to achieve desired formation properties.

A still further object of the present invention is to provide a method and apparatus for determining an electrokinetic property of a papermaking furnish by repeatedly measuring streaming potential of a single furnish sample.

An additional object of the present invention is to provide a method and apparatus of the character described which promotes desired web formation properties through control of papermaking furnish composition based on a measured electrokinetic property of the furnish.

Another object of the present invention is to provide a method and apparatus for accurately predicting the proportional amounts of charged additives required to optimize paper machine performance, including retention, drainage, and minimization of property variations.

Yet another object of the present invention is to provide a method and apparatus which obtains accurate information about streaming potential through a fibrous pad without the need to measure or apply specific pressure differentials across the pad.

SUMMARY

With regard to the foregoing and other objects, the invention provides an apparatus for determining an electrical characteristic of a papermaking furnish containing a dispersion of fibers. The apparatus includes a sample chamber for containing a sample of papermaking furnish. First and second sections of the chamber are separated by a fiber-collecting screen having a first side adjacent the first section of the chamber and a second side opposite the first side and located adjacent the second section of the chamber.

Means are provided for urging at least a portion of the furnish sample through the screen in alternating directions between the first and second sections of the chamber so that furnish flows back and forth through the screen in a plurality of cycles. During each cycle, furnish is moved through the screen in a first direction during a first period of time from the first section of the chamber to the second section of the chamber to form a pad of fibers adjacent the first side of the screen, and furnish is then moved through the screen in a second direction during a second period of time from the second section of the chamber to the first section of the chamber to push the pad of fibers from the screen to be redispersed in the furnish sample in the first section of the chamber.

The total time consumed in moving the furnish through the screen during the first and second periods of time equals one cycle period, which is preferably about two seconds.

Two electrodes are positioned within the sample chamber. The electrodes are electrically connected to a voltmeter which receives signals from the electrodes and produces a signal that corresponds to the potential difference between the electrodes at one or more points during each cycle period. Preferably, measurements are taken continuously during at least about five cycles and preferably about ten. The measurements are then statistically analyzed to provide a value or series of values over time indicative of an electrical characteristic, such as the initial value of streaming potential of the furnish, or the amount of a colloidally charged titrant required to change the streaming potential to a given target value.

In accordance with one embodiment, the means for urging furnish back and forth through the screen includes a variable volume chamber in fluid communication with the second section of the sample chamber. The variable volume chamber is preferably provided by a bellows which expands and contracts between a high volume state corresponding to the end of the first period of each cycle and a low volume state corresponding to the end of the second period of each cycle and the beginning of the first period. Accordingly, during transition of the bellows between low volume and a high volume state, fluid is urged through the screen from the first section of the chamber to the second section causing a pad of fibers to build up on the first side of the screen; and during transition of the bellows from the high back to the low volume state, fluid flow is urged through the screen from the second section of the chamber to the first section of the chamber causing the pad of fibers to be pushed off the screen into the first section of the chamber. The motive force for contracting and expanding the bellows may be provided by a simple relatively slow-rotating motor, the shaft of which carries a disc or crank arm with a link connected between the disc or crank arm and the bellows structure so as to provide a reciprocating contraction/expansion force on the bellows. Preferably the motor is of conventional speed with gears to reduce the speed of rotation so as to provide a reciprocating contraction/expansion force having a suitable cycle period.

Alternately, the means for urging flow back and forth through the screen may be provided by a motor-driven reciprocating piston sealably housed in an elongate cylinder connected in flow communication with the second section of the chamber and movable between high and low volume states as described above in connection with the bellows embodiment. As the piston transitions between the low volume and high volume states, fluid is urged through the screen from the first section of the chamber to the second section to build a pad of fibers on the first side of the screen. The pad of fibers is pushed off the screen into the first section of the chamber by fluid which is urged through the screen from the second section of the chamber to the first section of the chamber during transition of the piston between the high and low volume states.

In a further alternate embodiment, furnish may be urged through the screen by connecting the screen to a movable support member which sealably supports the screen in an elongate conduit for reciprocal movement between axially spaced-apart first and second positions therein. In effect, the screen becomes a piston which reciprocates in a cylinder (the elongate conduit) collecting the pad of fibers on its first side as it moves from the second to the first positions causing fluid to flow through the screen, and displacing the pad of fibers from the first side of the screen as it moves from the first back to the second position.

The apparatus may further include means for mixing furnish in the first section of the sample chamber to assist in the release and redispersion of the fiber pad from the screen and into the furnish sample. As a further feature, the apparatus may also include a water spray mechanism for rinsing and cleaning the sample chamber and screen after the plurality of a measurement cycles are completed.

The invention also provides a method for determining an electrical characteristic of a papermaking furnish containing a dispersion of fibers which comprises reciprocally urging the furnish back and forth from a first side of a fiber-collecting screen to a second side of the screen between first and second sections of a sample chamber located adjacent the first and second sides of the screen, respectively, during a plurality of cycles. During each cycle, fibers from the furnish build up to form a pad on the first side of the screen as furnish flows from the first to the second section of the chamber, and the pad is then pushed off the first side of the screen and the fibers thereof redispersed into the furnish in the first section of the chamber as fluid flow is reversed causing fluid to move from the second to the first section of the chamber. Thus, for each cycle, a single fiber pad is formed and expelled. A cycle period is the time consumed to complete one cycle. An electrical characteristic of the furnish sample is measured across each fiber pad as furnish moves through the screen.

The apparatus may be used in an investigatory/control mode to determine the effect of various additives on the properties of the furnish and to determine the amount of various additives needed to achieve desired properties in accordance with the methods and apparatus disclosed in commonly assigned copending application Ser. No. 08/995,668, filed Dec. 22, 1997, and entitled "Method and Apparatus for Determining Electrokinetic Properties of Papermaking Furnish" the subject matter of which is incorporated herein by reference. In general, this may be accomplished by connecting the sample chamber in flow communication with a source of charged additive. A suitable metering device is used to deliver measured amounts of additive to the furnish in a mixture with the assistance of a stirrer.

The invention therefore also enables determination of the endpoint of a titration in which a solution or colloidal dispersion, having a net positive or negative colloidal charge, is added to the sample in various ratios or in cumulative amounts. The procedure is carried out or repeated in a manner sufficient to determine the relative amount of titrant required to achieve a specific target or target values of streaming potential. Preferably the titrant is added to the sample at a constant rate. The amount of titrant corresponding to the target streaming potential may be determined by interpolation or linear regression. Preferably the target value equals zero, and the amount of titrant required to achieve the target value is called the net colloidal charge of the sample.

In one embodiment, once it is determined that a particular amount of titrant will bring the furnish to a desired endpoint, subsequent tests on the furnish may be undertaken with that amount of titrant as the target for the amount which should produce the desired endpoint. If addition of the amount of titrant brings the furnish to the desired endpoint, then the furnish is presumed to have the desired charge characteristics for proper formation and runnability. If addition of the amount of titrant does not bring the furnish substantially to the desired endpoint, then the amount of titrant necessary to provide the desired endpoint is determined and based on that amount, the composition of the furnish is adjusted and new samples are taken and tested with the titrant until the desired endpoint is reached with the original target amount. Of course, the desired endpoint should correlate with the desired web formation properties and runnability objectives, and the amount of titrant needed to bring the furnish to the desired endpoint may have to be redetermined periodically.

A significant advantage of the present invention is that it enables papermakers to accurately measure colloidal charge at the actual surface of the dispersed fibers based on a relatively rapid formation, dispersion and reformation of pads on a screen to produce a sinusoidal or wave-like representation of the electrical properties of the furnish. The measured value is substantially directly related to the surface charge of the fiber, not an estimation of the charge as provided by prior test devices. The usefulness of the charge measurements is substantially independent of the extent of compaction of the fiber pad. In addition, the test apparatus is greatly simplified over prior test devices since specific pressure differentials need not be applied across the pad.

The highly accurate and consistent results produced by the invention can be used by papermakers to control various aspects of the production process and maintain a more stable, uniform product. Quality, uniformity, and rate of production are all greatly improved as a result. The invention also promotes efficient use of furnish additives to achieve the desired formation properties.

BRIEF DESCRIPTION OF THE DRAWINGS

The above and other features and advantages of the invention will now be further described in the following detailed description in conjunction with the accompanying drawings in which:

FIGS. 7A and 7B are exemplary graphical illustrations showing how electrical potential measured across a fiber pad varies as a function of the position of a motor driving the bellows of FIGS. 1 and 2.

DETAILED DESCRIPTION OF A PREFERRED EMBODIMENT

Figure 1:
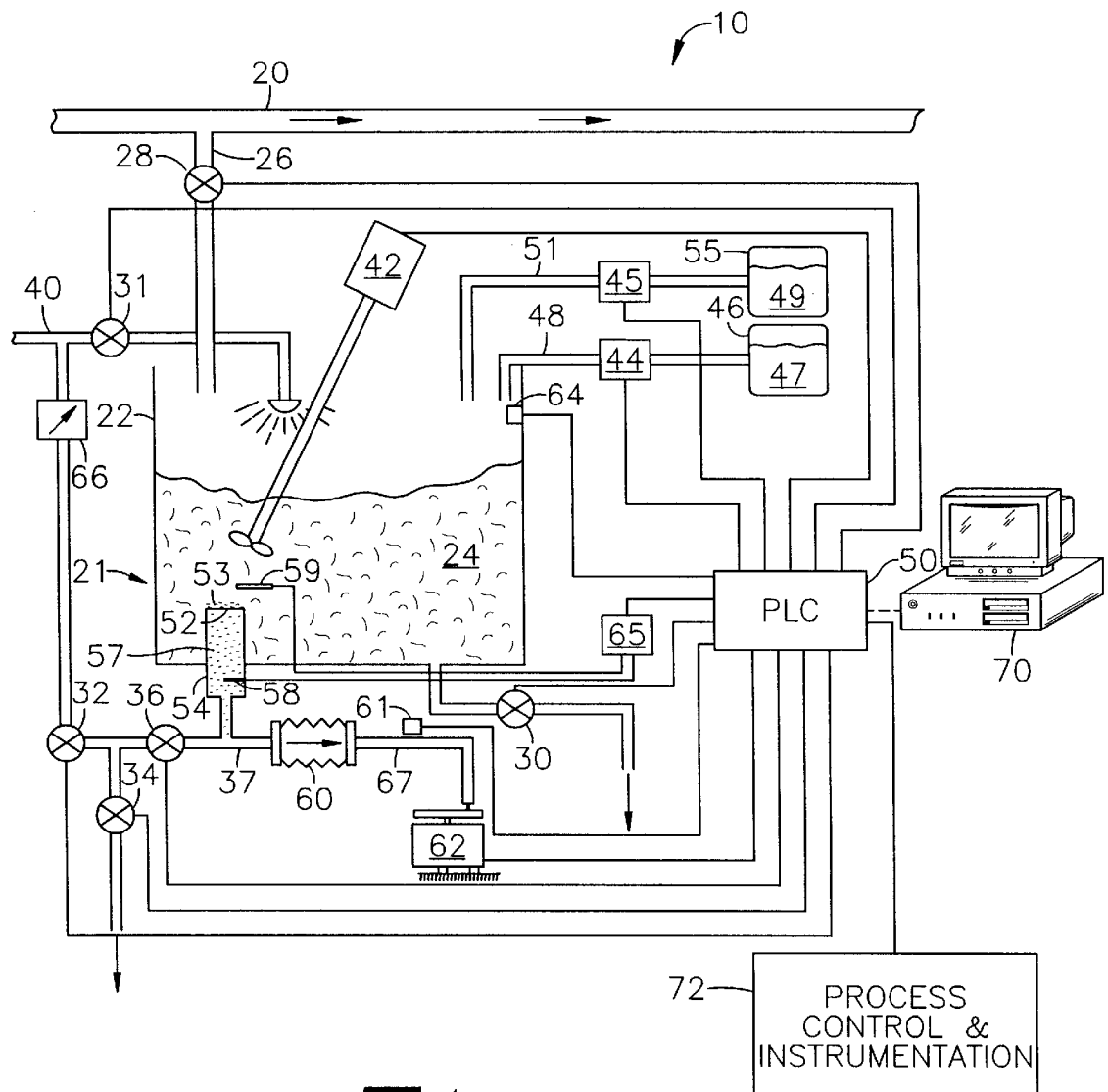
FIG. 1 is a diagrammatic view of a streaming potential measurement apparatus in accordance with one embodiment of the invention, showing a bellows at or near the end of its suction or pad-forming stroke.

With reference now to the drawings in which like reference characters designate like or similar parts throughout the several views, FIG. 1 illustrates an apparatus 10 for measuring an electrical characteristic of a sample 24 of wood pulp slurry or papermaking furnish. In general, this is achieved by urging furnish back and forth through a screen to repeatedly form and expel a pad of fibers onto and away from the screen. Streaming potential is measured across the screen during the forming and expelling of the fiber pad and used to determine an electrical characteristic, such as colloidal charge, of the papermaking furnish.

With reference to FIG. 1, during papermaking operations, papermaking furnish comprised of a dispersion of cellulosic fibers and various additives and other solids is conducted through a furnish conduit 20. A known amount of the furnish having a consistency in the range of about 0.02% to 5.00% is obtained from conduit 20, or elsewhere if desired, and placed in a sample chamber 21 where the furnish sample 24 is tested to determine an electrical characteristic of the furnish. A preferred range of furnish consistency is about 0.1% to 1.0% solids. In one aspect of the invention, the sign (i.e., positive or negative) of the electrical charge of the furnish is determined. In another aspect, the colloidal charge of particulates in the furnish is determined. The colloidal charge data is then processed to determine proportional amounts of charged additives required to optimize paper machine performance, including retention, drainage, and minimization of paper variations. In one embodiment, the apparatus 10 is automated and integrated with the paper machine itself to control the flow of a chemical additive which is mixed with the papermaking furnish to achieve optimal paper machine performance based on the colloidal charge data.

In general, papermaking furnish is an extremely complex and dynamic mixture. Because of the small size of the particulate matter (including fibers and other solids) contained within the furnish, the surface area per unit mass is enormous. Thus, processes involved in the formation of paper tend to be dominated by surface phenomena, particularly a phenomenon known as "double layer". For most types of papermaking furnish, the fiber surface will have a net negative colloidal charge such that the charged surface attracts ions of the opposite charge (i.e., counter-ions). These counter-ions are responsible for keeping the fibers dispersed. During papermaking operations, however, it is desirable to maintain the furnish charge at a stable level at each point in the process. For example it is desirable to maintain the colloidal charge of the furnish at the paper machine headbox within a narrow range of values. The optimum value of colloidal charge of furnish in the headbox may be negative, near zero, or positive, depending on details of the grade of paper, details of the process equipment, and details of the chemical additives.

While most or all of the steps involved in practicing the invention can be performed manually, it is preferable that the apparatus 10 be operated in a fully automated manner. For example, while the furnish sample 24 can be obtained manually from production stock, it is preferable that furnish be automatically diverted from some point in the furnish production process, such as a furnish flow conduit 20, and into the sample chamber 21 by way of a sample conduit 26 and sample valve 28.

In a preferred embodiment of the present invention, automation is achieved through use of electronic control devices, such as a programmable logic controller (PLC) 50. Preferably, PLC 50 is a programmable logic controller manufactured by Allen-Bradley of 1201 South Second Street, Milwaukee, Wis. 53204 under model no. SLC 500™. If desired, a personal computer 70 can be linked to the PLC for PLC programming, data transfer, optional operation of the device in a semi-manual mode, and when necessary, to perform diagnostic functions.

An individual measurement begins when an operator or the PLC 50 opens sample valve 28 to admit a known amount of papermaking furnish into the sample chamber 21 from conduit 26. Sample chamber 21 includes a first section 22 preferably defined by an open-top container and separated from a second section 54 by a screen 52. In accordance with a preferred embodiment, second section 54 is defined by apparatus closing the area on the side of the screen 52 opposite that of the first section 22 as will be hereinafter described in more detail.

Preferably, the first section 22 is open to the atmosphere as shown in FIG. 1, but it may also be closed. For example, the first section 22 may be a closed-top container connected to a source of compressible gas, or to a column of furnish contained in a sample line. Preferably, furnish sample 24 is taken from a sample point which faithfully represents the composition, percent solids, and other attributes of furnish present within the headbox or pulp vat of a paper machine. Alternatively, the sample may be diluted. It is preferred to dilute pulp samples or blended furnish samples in those cases where the ordinary level of fiber is too high to facilitate efficient mixing of a titrant with the sample. For example, in another embodiment, the apparatus may be used to monitor the colloidal charge of hardwood or softwood chemical pulps, mechanical pulps, broke, or recycled pulps, wherein dilution from about 4.0% solids or more to a range of about 0.1 to 0.5% solids facilitates mixing. A proximity sensor 64 detects when the furnish sample 24 reaches a desired level within the sample chamber 21, and a signal is output by the proximity sensor 64 to the PLC 50 which shuts off sample valve 28 in response to the proximity sensor output. A known amount of furnish sample 24 is now contained in the first section 22 of the sample chamber 21 and ready to be measured.

Suitable proximity sensors for use with the invention include conductivity sensors, optical sensors, capacitance sensors, float switches, and the like. Alternatively, or in combination, the fill level of sample chamber 21 may be achieved by providing a suitable overflow port. In one embodiment, the proximity sensor acts sufficiently promptly to avoid overflowing the sample chamber 21, but the fill level is effectively controlled by overflow of any excess of sample 24. As another alternative, the measurement could be carried out with an arbitrary volume of furnish with the volume or weight of the sample being determined later. The measurement may also be carried out without regard to sample volume or consistency as a means of simply determining the sign of streaming potential.

A variable volume chamber, such as a bellows 60, forms part of the second section 54 so that as the volume of the bellows 60 varies, the volume of the second section 54 also varies. When the volume of bellows 60 is increased, the pressure on the side of the screen 52 adjacent the second section 54 becomes less than the pressure on the opposite side of the screen 52, thereby causing furnish to flow through the screen 52 from the first section 22 to the second section 54. In similar fashion, when the volume of bellows 60 is decreased, the pressure on the side of the screen 52 adjacent the second section 54 becomes greater than the pressure on the side of the screen 52 adjacent the first section 22, causing filtrate 57 contained in the second section 54 to flow through the screen 52 into the first section 22 and releasing the pad 53 from the screen 52. Thus, when the volume of bellows 60 is repetitively increased and decreased, furnish 24 contained within the sample chamber 21 is urged back and forth through the screen 52 between the first and second sections 22, 54 of the sample chamber 21 so that fluid within the furnish is cycled through the screen 52 to repetitively form and expel the fiber pad 53 during a series of cycles.

In order to vary the volume of the bellows 60, various mechanisms known to those of ordinary skill may be used including a slow-rotating motor 62 connected to the bellows 60 by crank arm 67 in a way which causes fluid to be moved bi-directionally through the screen 52 during rotation of the motor shaft, thereby repetitively forming and expelling a fiber pad 53 where each fiber pad 53 is formed from fibers and particulates suspended within the furnish sample 24. It is understood that the effect of a slow rotating motor may be achieved by a suitable gear reduction of a rapidly rotating motor. In an alternate embodiment described hereinafter, the fiber pad 53 is formed and expelled during the cycles by reciprocating the screen 52 within the furnish sample 24.

During each cycle, furnish is moved through the screen 52 from the first section 22 to the second section 54 to form the fiber pad 53 on the side of the screen 52 which is adjacent the first section 22 with the filtrate 57 at least partly filling second section 54, and furnish is then moved back through the screen 52 from the second section 54 to the first section 22 to expel the pad 53 from the screen 52 to be redispersed in the furnish sample 24 in the first section 22 of the sample chamber 21. The bellows 60 is preferably substantially impermeable to the flow of liquid and electric current over the whole of its surface. Likewise, the second section 54, which includes the bellows 60 as part of its variable enclosed volume, is preferably substantially impermeable to the flow of liquid and electric current over the whole of its surface with the exception of the screen 52 during the period of time when a measurement or measurements are in progress.

If desired, the walls of the second section 54, including connecting tubing 37, may be fabricated from a resilient material. The effect of these resilient elements is to modulate or limit any occurrences of excessively high pressure differentials across the screen 52 which might otherwise tend to damage the screen 52, second chamber section 54, or bellows 60. The bellows 60 may also be fabricated of a resilient material to limit pressure. Pressure limiting may further be achieved by including within the second chamber section 54 a volume of compressible fluid such as air, either in contact with the filtrate 57 or enclosed in a flexible container such as a balloon. Alternatively, a suitable resilient element may be connected to extend the effective bounded volume of second section 54 in such a way that excessive relative pressures are avoided. Alternatively, the bounded volume of the second section 54 may be connected to an air-fed pressure relief valve, air-bleed valve, or combination of a bleed valve and a pressure relief valve to guard against excessive mechanical strain on the system, with the limitation that the amount of leakage is not so great as to defeat the function of the device.

Screen 52 may be fabricated from a variety of materials, including metals, plastics, and porous membranes or fabrics. In a preferred embodiment, screen 52 is a perforated stainless steel sheet and is positioned between the first and second sections of the sample chamber 21 in such a manner that relatively little or no fluid is allowed to flow around the screen 52 from the first chamber section 22 into the second chamber section 54. The screen 52 has a mesh of suitable size to enable passage of aqueous fluid yet inhibit passage of a substantial portion of the suspended particles (including fibers, fillers, etc.) in the furnish sample 24 to substantially simulate the capture of such materials on the forming fabric of a papermaking machine. Perforations sufficient to accomplish this objective preferably have a truncated conical cross-section. The side of the screen having the smaller diameter openings is presented toward the furnish sample 24. On the furnish side of the screen 52, the openings have a diameter in the range of from about 50 $\mu$m to about 500 $\mu$m, providing a total fraction of open area in the range of about 10 to 50 percent of the total screen surface area. In an alternative embodiment, the screen 52 is a plain-weave stainless steel or plastic screen, most preferably within a range of standard mesh sizes between 20 $\mu$m and 200 $\mu$m.

Two electrodes 58, 59, preferably positioned on opposite sides of the screen 52, are employed to measure streaming potential as the fiber pad 53 is forming and/or being expelled and fluid is flowing through the fiber pad 53 or screen 52. Accordingly, electrode 59 may be positioned in the first section 22 on the pad-forming side of a screen 52 within the filled part of first section 22, and electrode 58 may be positioned in the second section 54 on the opposite side of the screen 52.

In some applications, however, it may be desirable to place both electrodes in the same section of the sample chamber 21, such as first section 22, or to place one electrode in the first section 22 and to connect and/or incorporate the other electrode to or into the screen 52. In a preferred embodiment, the electrodes are fabricated from a silver alloy wire having a molecular composition of 45% silver, 30% copper, and 25% zinc. This silver alloy represents a class of oxidizable metal materials which have been found to minimize the effect of signal drift commonly associated with electrodes employed in streaming potential measurement devices. An alternative way to minimize signal drift is through the use of reversible reference electrodes having a liquid junction or other type of junction to isolate a half-cell such as in a calomel electrode or silver-silver chloride reference electrode. Alternatively, it is possible to carry out measurements as described by using electrodes comprised of gold, platinum, or stainless steel.

As a further means of minimizing the effect of signal drift, it has been found advantageous to calculate each sequential datum of streaming potential in the following manner. A peak voltage value is determined corresponding to an average of measured signals obtained when a fiber pad 53 has substantially accumulated on the screen 52. Two corresponding background voltage values are obtained from the adjacent periods of time when the furnish is moved in the second direction and there is no substantial pad 53 present on the screen 52. The streaming potential is then identified with the difference between the peak voltage and half of the sum of the two background voltages. In addition, the effects of signal drift tend to be minimized by the relatively rapid repetition of cycles of collection and explusion of fiber pads 53.

The reciprocating flow of fluid through the screen 52 causes a change in the electrical potential measured with electrodes 58, 59 which can be recorded continuously during the cycles. The measured voltage obtained as fluid is flowing through the pad 53 is compared with the voltage values obtained after the pad 53 has been expelled from the screen 52, and the difference between the two voltages corresponds to the streaming potential of the furnish.

As an alternative embodiment, it is feasible to base the analysis on data obtained during parts of the cycle differing from or not specifically associated with the maximum build-up of the pad 53 or the absence of pad 53 near the end of the expulsion stroke. For example, an indication of the magnitude of streaming potential may be achieved by determining the standard deviation among voltage measurements obtained at random or non-synchronized times during a plurality of cycles. In another illustrative case, it is feasible to base an analysis of relative values of streaming potential on data collected at two or more points of time during the progressive build-up of a fiber pad 53 during one or more cycles.

The electrodes 58, 59 are preferably positioned so they are not in contact with the fiber pad 53 or screen 52. The outputs of the electrodes 58, 59 are provided to an electrical potential measuring device, such as a direct-current millivolt meter 65, which determines the potential difference between the electrodes 58, 59 as well as the sign and magnitude of streaming potential. The output of meter 65 is provided to the PLC 50 which routes measurements to process control and instrumentation 72 and/or computer 70 where the streaming potential measurements may be used by process control personnel to monitor and control the colloidal charge of papermaking furnish accordingly.

In an alternate embodiment, the function of electrode 58 may be replaced by a screen 52 made of a suitable electrically conductive material. Additionally, the functions of meter 65 alternatively may be incorporated into the PLC 50.

Figure 2:
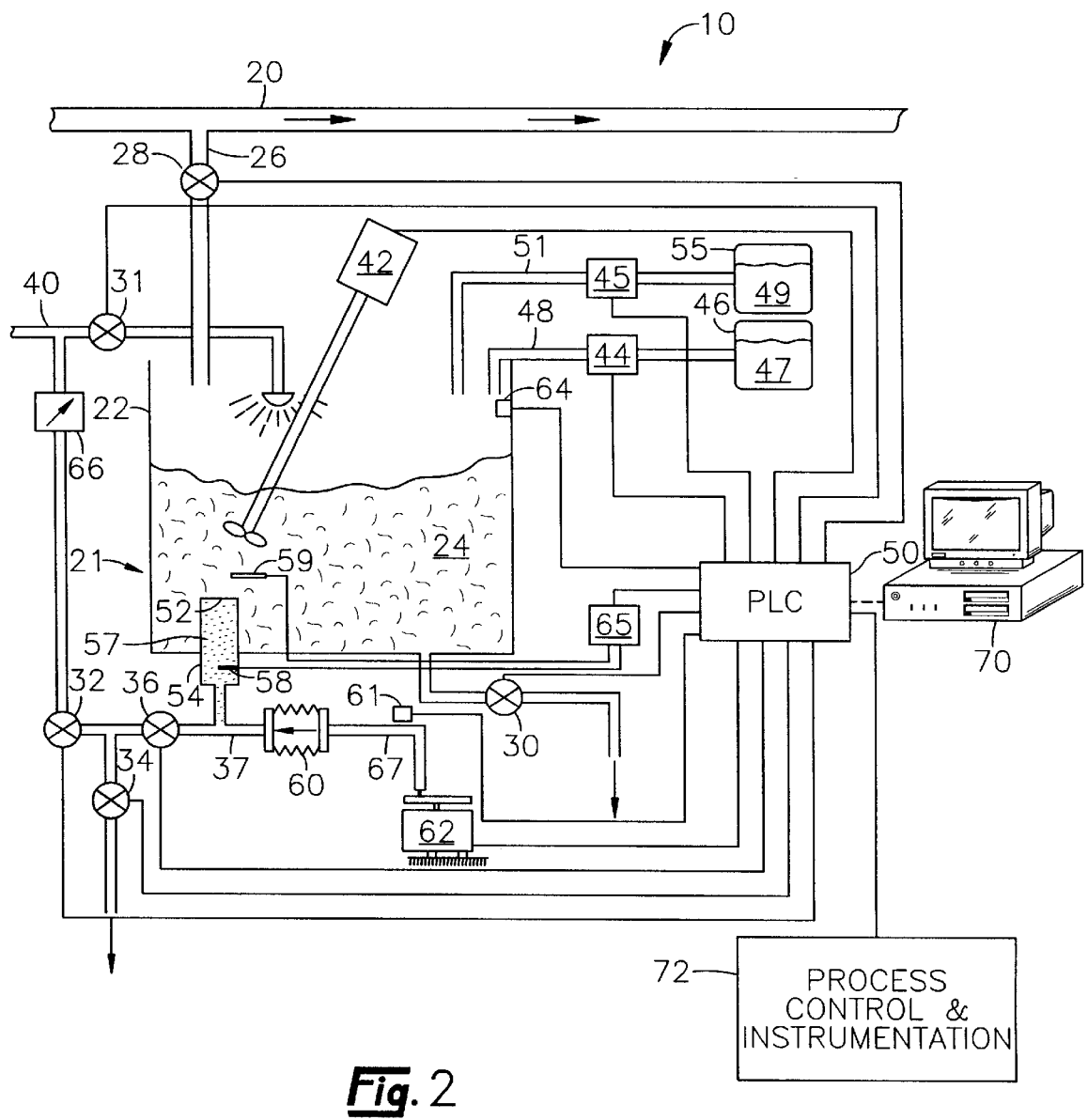
FIG. 2 is a diagrammatic view of the streaming potential measurement apparatus of FIG. 1 with the bellows shown at or near the end of its expulsion stroke.

With a known amount of fiber furnish contained within the sample chamber 21, the apparatus 10 may be operated during an initial measurement period to determine the sign of the colloidal charge of the papermaking furnish and to enable the electrodes 58, 59 to achieve a state of equilibrium. During the initial measurement period, the PLC 50 outputs a signal to initiate the impeller stirrer 42. Motor 62 is also initiated by the PLC 50 to drive bellows 60 in a reciprocating manner. As shown in FIGS. 1 and 2, the bellows 60 is in communication with the furnish sample 24 with screen 52 being positioned intermediate the furnish sample 24 and bellows 60 in such a manner that furnish is moved through the screen 52 to form the fiber pad 53 during the suction stroke (FIG. 1) of the bellows 60, and the fiber pad 53 is expelled from the screen 53 during the expulsion stroke (FIG. 2) of the bellows 60. The voltage across the screen 52 is measured, preferably continuously, as the furnish is moved back and forth through the screen 52 to form and expel the fiber pad 53.

As previously described, the electrodes 58, 59 are made of a silver alloy to reduce the effect of signal drift. The effect of signal drift is further minimized by cycling the bellows 60 at a relatively rapid rate where each cycle of the bellows 60 includes a suction stroke and an expulsion stroke. In a preferred embodiment, the cycle period is two (2) seconds (i.e., the bellows 60 is expanded and contracted by motor 62 every two seconds, during which time a single fiber pad 53 is formed and expelled from the screen 52). This relatively rapid cycling of the bellows 60 also enables the apparatus 10 to provide, among other things, a precise indication of the sign of charge.

Figure 3:
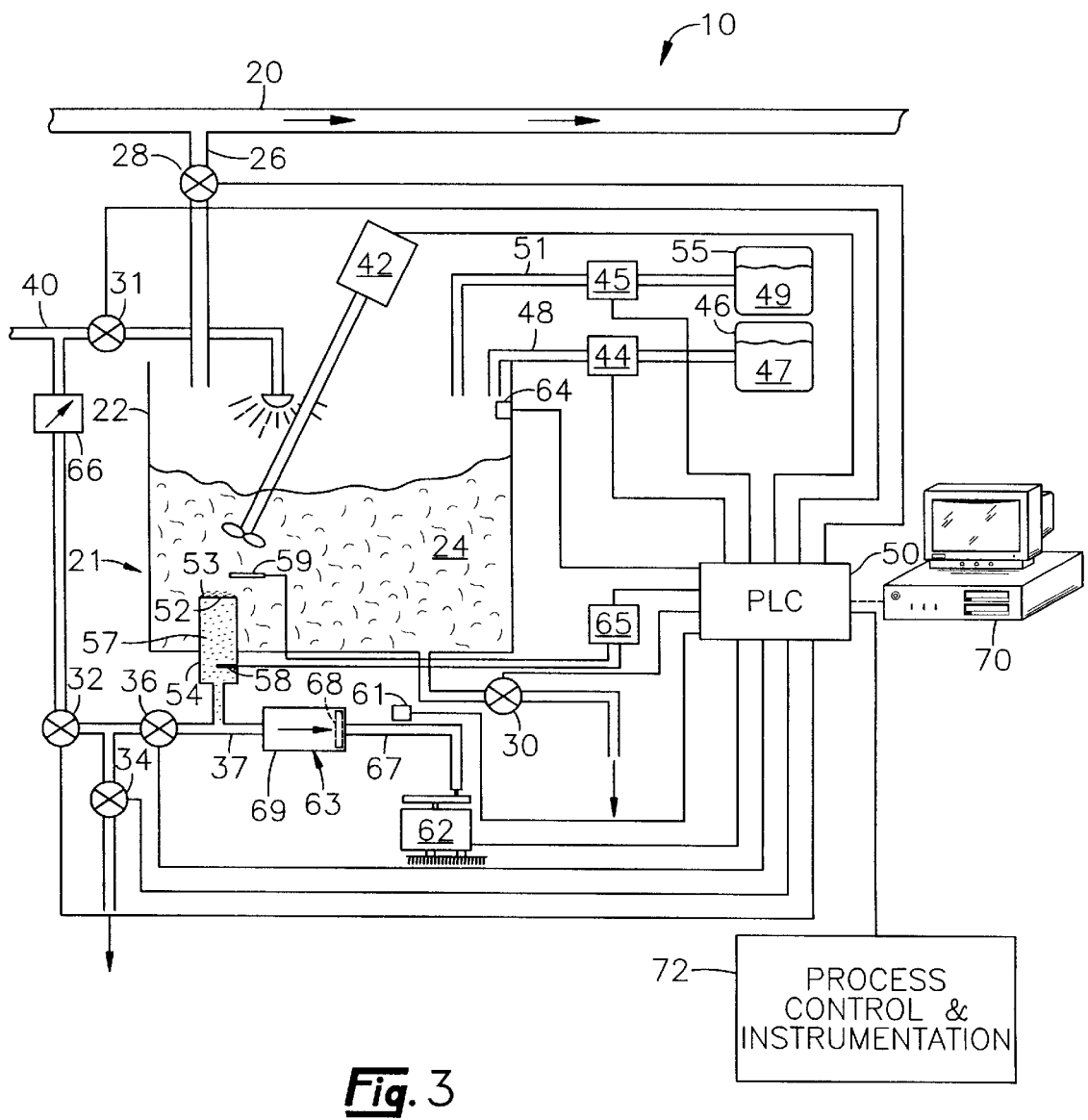
FIG. 3 is a diagrammatic view of a streaming potential measurement apparatus in accordance with an alternate embodiment of the invention, showing a piston chamber at or near the end of is suction or pad-forming stroke.
Figure 4:
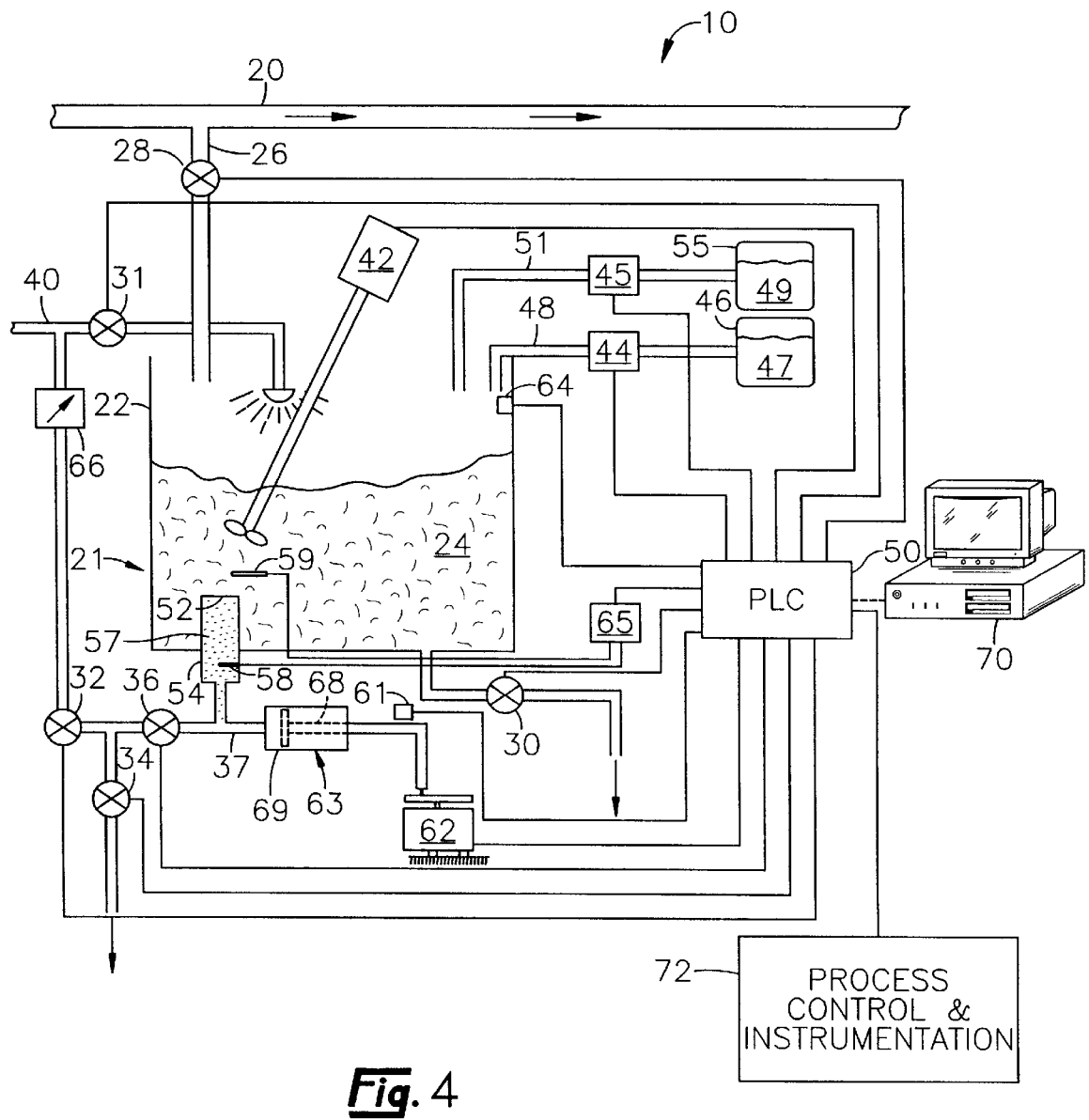
FIG. 4 is a diagrammatic view of the streaming potential measurement apparatus if FIG. 3 with the piston chamber shown at or near the end of its expulsion stroke.

In an alternate embodiment of the invention shown in FIGS. 3 and 4, the bellows 60 is replaced by a piston pump 63. The piston pump 63 includes a piston 68 sealably reciprocable in a cylinder 69 and reciprocably driven by crank arm 67. As the piston 68 is moved by crank arm 67 to a retracted position as shown in FIG. 3, the volume of second section 54 increases and causes pressure in the second section 54 to become less than pressure in the first section 22. Resultingly, furnish is urged through the screen 52 from the first section 22 to the second section 54 and a pad of fibers 53 forms on the screen 52 as described above with reference to FIG. 1. When the piston 68 is moved by crank arm 67 to an extended position as shown in FIG. 4, pressure in the second section 54 becomes greater than pressure in the first section 22 causing filtrate 57 in the second section 54 to be urged back through screen 52 from the second section 54 to the first section 22. The flow of filtrate 57 through the screen 52 into the first section 22 causes the fiber pad 53 to be expelled from the screen 52 back into the first section 22 where the pad 53 is redispersed in the furnish sample 24 by stirrer 42.

Figure 5:
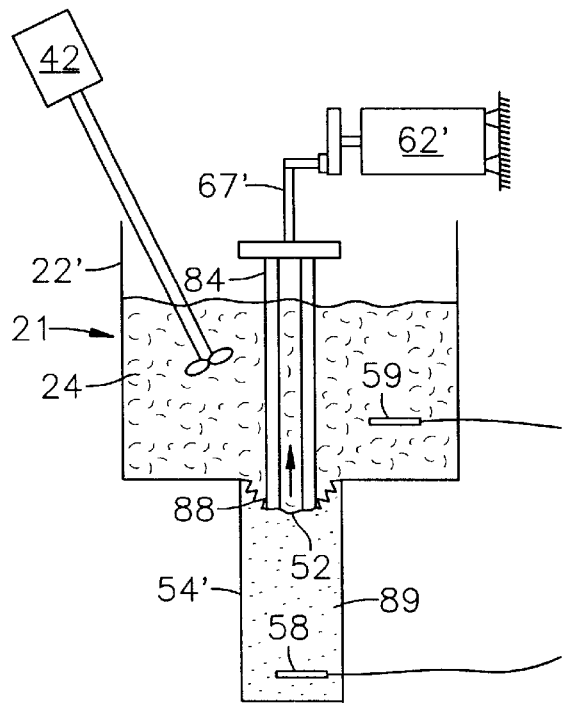
FIG. 5 is a side view of an apparatus for measuring streaming potential in accordance with another embodiment of the invention showing a reciprocating screen at or near the end of its expulsion stroke.
Figure 6:
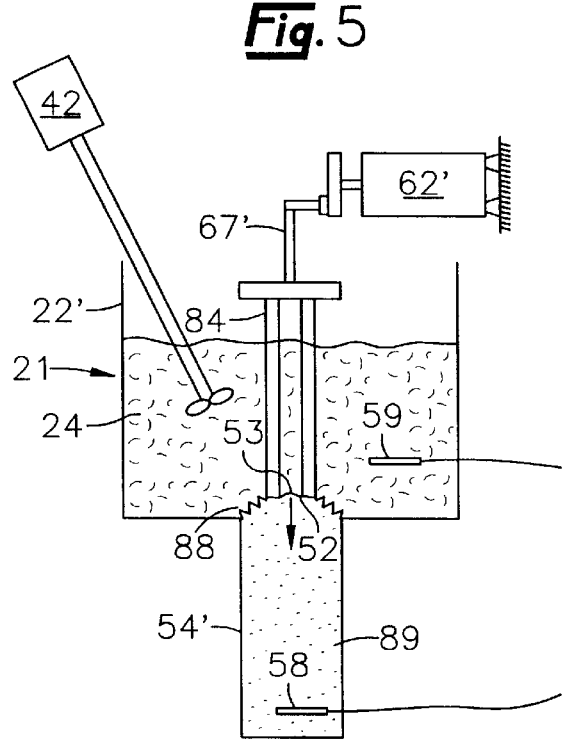
FIG. 6 is a side view of the apparatus of FIG. 5 with the reciprocating screen shown at or near the end of its pad-forming stroke.

In a further alternate embodiment of the invention shown in FIGS. 5 and 6, sample chamber 21' includes a first section 22' preferably defined by an open-top container separated from a second section 54' by a screen 52 and a flexible or extensible fluid-impermeable collar 88. The flexible collar 88 is attached at one end to the perimeter of the screen 52 and at the other end is attached to the annular opening of the second section 54' to confine any fluid flow between the first and second sections 22' and 54' to flow through the screen 52. The screen 52 is supported within the furnish sample 24 by a support member 84 which in turn is connected to a motor 62' by crank arm 67' so that as the shaft of motor 62' is rotated to drive the crank arm 67' and support member 84 in an up and down motion, a fiber pad 53 is repetitively formed on the screen 52 and expelled back into the furnish sample 24 in cycles as the screen 52 reciprocates within the furnish sample 24.

With continued reference to FIGS. 5 and 6, as the screen 52 is moved up and out of first section 22', the effective volume of the second section 54' increases and causes the pressure on the side of the screen 52 adjacent the second section 54' to decrease relative to the pressure on the side of the screen 52 adjacent the first section 22'. The resulting pressure differential urges a flow of furnish 24 from the first section 22' through the screen 52 and into the second section 54'. As a result, a pad of fibers 53 is formed on the side of the screen 52 adjacent the first section 22'. Furnish which has passed through the screen 52 is collected in second section 54' as filtrate 89.

As the screen 52 is moved down during the expulsion stroke of the motor 62', the effective volume of the second section 54' decreases and pressure on the side of the screen 52 adjacent the second section 54' becomes greater than the pressure on the side of the screen 52 adjacent the first section 22'. As a result, filtrate 89 is urged back through the screen 52 from the second section 54' to the first section 22' and expels the fiber pad 53 from the screen 52 and into the furnish sample 24 where the pad 53 is redispersed by a stirrer 42. Electrodes 58, 59 record the voltage difference during a plurality of pad-formation, expulsion cycles as described above.

To achieve a desired colloidal charge level in the furnish or test the effect of certain additives, various chemical additives may be introduced into the furnish in the practice of the invention. The degree to which the fibers take up each type of additive is directly dependent on the capacity of the fiber's double layer, or in other words, the fiber's cationic or anionic demand (for anionic or cationic furnish as the case may be). For additives like starch, sizing agents, and retention aids to perform well and consistently, the charge should be as stable as possible.

In one application of the invention, the above-described apparatus and method in its various embodiments may be used to determine the colloidal charge of the furnish by titrating the furnish sample 24 with a charged additive for investigating the effect of various additives and to control the formation properties of the paper on the machine as described in the aforementioned commonly assigned application Ser. No. 08/995,668 filed on even date herewith. Thus, with reference to FIG. 1, a positively charged (catonic) titrant 47 supplied by titrant reservoir 46 or a negatively charged (anionic) titrant 49 supplied by titrant reservoir 55 may be added until the apparatus 10 indicates that the streaming potential has reached a predetermined level, or endpoint. In general, colloidal charge is determined by titrating the furnish sample 24 with a charged additive and measuring the streaming potential of the furnish sample 24 across successive fiber pads 53 formed on screen 52 (as described above) until streaming potential across the screen 52 reaches a desired endpoint or has been satisfactorily characterized. In most cases the desired streaming potential endpoint after adjustment with the titrant will be zero (neutral).

Accordingly, in one embodiment of the invention, colloidal charge is determined by the apparatus 10 based on the amount of titrant 47 needed to exactly neutralize the charge of the furnish sample 24 or bring its streaming potential to zero. The colloidal charge data may then be used to automatically control the flow of one or more charged additives to keep the colloidal charge of the papermaking furnish within a very narrow range, and thus, stable. With the colloidal charge stable, various runnability and property targets can be optimized by adjusting the colloidal charge (i.e., by adjusting the amount of charged additives) as needed.

Examples of charged additives, or titrants 47, 49, which may be used in accordance with the invention include polydimethylamine epichlorohydrin (polyamine), polydiallyldimethylammonium chloride (DADMAC), poly-amidoamine-epichlorohydrin resin (PAE), poly-aluminum chloride (PAC), aluminum sulfate (papermaker's alum), potassium polyvinylsulfate (PVSK), colloidal silica, bentonite, carboxymethylcellulose (CMC), copolymers of acrylate and acrylamide, and others.

As described above, the apparatus 10 in a titration or investigatory mode may be operated during an initial measurement period to enable the electrodes 58, 59 to stabilize and to ascertain the sign of colloidal charge of the furnish sample 24. The sign of colloidal charge (i.e., positive or negative) may then be used to select the proper type of titrant 47, 49 to be used during titration of the furnish sample 24. If the initial measurement results indicate that the furnish sample 24 exhibits a positive (cationic) colloidal charge, a negative (anionic) titrant 49 will be used during titration. A cationic titrant 47 is used when initial measurement results indicate a negative colloidal charge in the furnish sample 24.

It will be understood that the initial measurement is not necessarily required in order to determine which type of titrant 47, 49 to be used for the titration process. Other methods may be used to determine the proper type of titrant 47, 49 required for titration. For example, a titrant 47, 49 may be arbitrarily selected initially. If steaming potential measurements indicate that the colloidal charge is moving away from zero, then the wrong titrant was selected. If measurements indicate that colloidal charge is moving toward zero, then the proper titrant was selected.

The titrant 47, 49 may be added either continuously or incrementally. In a preferred embodiment, the titrant is added by means of a metering pump 44, 45 having a capacity in the range of about 0.25 ml to 10.0 ml per minute. It is most preferred to alternate each titrant pump 44, 45 between two alternative states corresponding to zero flow or a constant rate of flow such as 1.5 ml/min. A constant rate of titrant flow is seen as a way to simplify interpretation of the results. In an alternative embodiment the rate of delivery is adjusted by an algorithm programmed into the PLC 50. The algorithm adjusts the rate of titrant delivery based on the results achieved up to that point. For example, after the initial measurement period of zero titrant flow, a small increment of titrant 47, 49 (such as one drop) is added to the furnish sample 24. If the streaming potential measurement value shifts by less than five percent relative to its initial value, then the next increment is increased by a factor of two. The titration is continued in this manner until the measurements approach zero. At that point, the size of each increment may be decreased to a degree which will improve the precision of the endpoint. Alternatively, a similar algorithm may be used to improve the time-efficiency and precision of titrations carried out with an essentially continuous or pulsating flow. In another embodiment, the flow of titrant 47, 49, once it is started, proceeds at a constant rate.

Following the initial measurement, the appropriate titrant pump 44 or 45 is initiated by the PLC 50, and a signal from the PLC 50 starts a metered flow of the titrant 47 or 49 into the sample chamber 21 where the titrant is mixed with the furnish sample 24 by the action of the impeller stirrer 42. Assuming the initial measurement indicates the furnish sample 24 is negatively charged, the highly charged cationic titrant 47 will be selected by the PLC 50 for titration. The titrant 47 interacts with colloidal material in the furnish sample 24 and at the surface of the suspended solids. Some of the titrant 47 gradually is absorbed into the fiber walls. The relatively rapid, automatic titration and prompt data collection of the PLC 50 help to ensure that this tendency does not compromise the precision of the measurements. As titrant 47 is mixed into the furnish sample 24, the measured difference in oscillating electrical potential becomes less and eventually reaches zero. The elapsed time and volume of titrant required to reach the desired streaming potential endpoint is processed by the PLC 50 and sent to a user interface and/or process control computer, shown generally in FIGS. 1 and 2 as process and control instrumentation 72, where the processed measurements are displayed.

In a preferred embodiment, titrant 47 is delivered to the sample chamber 21 by means of a metering pump 44 having a delivery per stroke of approximately 0.05 ml volume. Examples of pumps capable of delivering this volume include a Barnant model HD-MA-CC, type M250 with Teflon™ diaphragm having a rated output per stroke of 0.04 ml. One advantage is that this type of pump will tend to deliver one drop with each stroke. Such a delivery rate is a compromise between precision (favoring a flow large enough to meter precisely) and convenience (favoring a minimum usage rate of liquid titrant 47 and minimum likelihood that the outlet of the titrant line 48 should become clogged with solid matter from the furnish sample 24). Also, by having the outlet of the titrant delivery lines 48 above the fill level of the sample chamber 21, it is easier to verify and calibrate the flow of titrant 47 during operation of the apparatus 10. Although a pump which delivers one drop of titrant 47 per stroke is preferred, it will be understood that a larger output per stroke could be used instead. Alternatively, the outlet ends of delivery lines 48 and 51 may be provided with fine nozzles to decrease the size of the resulting droplets.

Colloidal charge is calculated based on the volume of titrant required to bring the furnish sample 24 to its streaming potential endpoint and the amount of sample (i.e., the percent solids, assuming a constant sample volume). Specifically, colloidal charge is determined by multiplying the volume of titrant required to reach the desired titration endpoint by the concentration of the titrant, and then dividing the product by the volume of the furnish sample 24. To take best advantage of this information, the data is used by papermakers to control the flow of one or more charged additives so that the colloidal charge is maintained within a narrow range. Since paper production typically requires the optimization of several different runnability and property targets at the same time, it is extremely difficult to select the best value of colloidal charge a-priori. Once colloidal charge is highly stabilized in accordance with the invention, however, then colloidal charge can be more readily optimized and controlled.

Preferably, the furnish sample 24 is acquired at some point in the furnish production process at or near the headbox. Obtaining the furnish sample 24 at or near the headbox is an ideal sample point because the furnish at that point is typically low enough in solids to permit rapid, thorough mixing with the titrant 47, and because the results will generally show the net effect of all the pulp streams and additives. Although a preferred embodiment of the invention uses a titration endpoint of zero potential, the optimum value of colloidal charge cannot be predicted theoretically. Rather, the goal is to determine the value which yields the best combination of retention, drainage, and product quality. Once that value is determined, the invention may be employed to perform the necessary measurements and to make the necessary adjustments with charged additives (such as polyamines, PEI, PAC, etc.) to keep it there. If desired, the apparatus 10 can also be employed to perform off-line measurements of a component stream such as broke or various pulp streams such as de-inked or kraft pulp.

Although the titration and investigatory aspects of the invention have been described with respect to FIGS. 1–4, it will be understood that such features may find application in all embodiments of the invention including, but not limited to, that of FIGS. 5–6.

After a measurement or series of measurements has been made, the PLC 50 preferably initiates a series of operations to automatically drain and clean the sample chamber 21, impeller stirrer 42, screen 52, and other elements of the apparatus 10 in preparation for the next measurement. Thus, with reference to FIGS. 1–2, valve 30 may be opened to drain the titrated sample 24 from the sample chamber 21. Valve 31 opens to rinse the sample chamber 21 with water supplied by conduit 40. Preferably, water is sprayed by a nozzle 38 until proximity sensor 64 indicates that the sample chamber 21 is full. The impeller stirrer 47 is operated for a period of time to thoroughly rinse the sample chamber 21. Water is also routed from conduit 40 into the bellows 60 and second chamber section 54 by opening valves 32 and 36. Motor 62 is turned on to operate the bellows 60 as fresh water is cycled to rinse the bellows 60. Alternatively, either the spray water or water used to rinse the bellows 60 and second section 54 may be replaced by a suitable nonionic surfactant solution. For example, a 200 ppm solution of Triton-X 100 surfactant may be used to rinse various parts of the apparatus. In such cases it is preferred to carry out a further rinse with water. A pressure regulator 66 is employed to prevent damage to the bellows 60 or other equipment due to high pressure water which might be present in conduit 40. After the bellows 60, sample chamber 21, and other equipment have been rinsed, valves 30 and 34 open to drain the rinse water from the apparatus 10. Of course, the same rinse mechanisms and procedures may be used with all embodiments of the invention including those of FIGS. 3–6.

The following nonlimiting example further illustrates various aspects of the invention.

EXAMPLE 1

A test was performed in order to demonstrate the basic operation of the invention and its ability to accurately determine streaming potential and sign of streaming potential. The test apparatus corresponded to the embodiment of FIGS. 1–2 and included a sample chamber 21 consisting of a polymethylmethacrylate cylinder having an inner diameter of 5.75 inches and a wall thickness of ⅛ inches. The cylinder was permanently attached onto a PMMA base disk of ½ inch thickness. The center of the base disk was machined and threaded to accommodate a filter screen 52 of type 60K from Paper Research Materials, Inc. of Gig Harbor, Wash. The diameter of the screen was cut to one inch. The screen was provided with holes of conical cross-section of diameter 250 $\mu$m, with a net open area of 32.5%. The smaller ends of the openings were oriented toward the first section of the sample chamber during testing. The screen had an exposed diameter of ¾ inch, and was held in place with an O-ring. A threaded plastic coupling was screwed into the base plate to hold the O-ring and screen in place.

The electrode probes 58, 59 were fashioned from Silvaloy™ A45 welding wire having a diameter of ⅛ inch. Cut ends of the welding wire were rounded and burnished. For sensing the relative electrical potential in the sample chamber, the end of a seven-inch section of the welding wire was shaped into a circle of diameter 1.5 inches. The last straight three-inch section of wire was bent 90 degrees with respect to the circle. The probe 59 was inserted into a drilled hole in the base plate and sealed so that the circle was held ½ inch above the base plate. A second electrode probe 58 was a single straight one-inch section of the same alloy wire. It was inserted and sealed into a hole cut into the threaded plastic coupling.

The plastic coupling was attached by means of a barbed tubing connector and a Tygon™ tube to the tubing connector of an Iwaki Walchem bellows pump (model number SP20-20) having a full stroke capacity of 10 ml and a stroke cycle period of 1.8 seconds (33 rpm). The bellows pump 60 was set to run at full stroke. The check valves were removed. The check valve which was not connected to the sample chamber was blanked off with a solid rubber gasket.

A sample of 100 ml of 4% solids slurry of de-inked kraft pulp was diluted with 1000 ml of distilled water to a consistency of about 0.4%. The conductivity of the sample was approximately 200 $\mu$S/cm. The pulp was continuously stirred with an impeller stirrer 42. A Fluke™ multimeter was attached to the respective electrodes 58, 59. The positive lead (red) was attached to the electrode 59 in contact with the furnish sample 24 in the first section 22 of the sample chamber 21. It was observed that the measured signal varied in a systematic way corresponding to the period of reciprocating motion. The highest values (most positive) were observed when the bellows 60 had just reached its most contracted position (FIG. 2). The lowest values were observed when the bellows 60 had just reached its most expanded position (i.e., the pad was fully formed)(FIG. 1).

FIG. 7A is a graphical illustration of motor position during two consecutive, two-second cycles of the motor 62 where motor position is graphically shown as being at a value of "−1" (90 in FIG. 7A) when the crank arm 67 is at top dead center and the bellows 60 is fully expanded and at the end of the pad-forming stroke (FIG. 1), and the motor 62 is positioned at a value of "+1" (92 in FIG. 7A) when the crank arm 67 has moved 180 degrees from top dead center 90 and the bellows 60 is fully contracted and at the end of the expulsion stroke (FIG. 2). FIG. 7B is a graphical illustration of voltage measured across the screen 52 during the same two cycles shown in FIG. 7A.

From a comparison of FIGS. 7A and 7B, it can be seen that voltage across the screen 52 during the expulsion stroke (98 in FIG. 7B) is relatively stable during most of the expulsion stroke (94 in FIG. 7A), which occurs during the first second of each cycle. During the pad-forming or suction stroke, shown in FIG. 7A at 96, the voltage signal 98 increases to a peak 100 at about 1.75 seconds into the cycle as the fiber pad 53 forms. As the motor 62 nears the end of the suction stroke, the voltage across the screen 52 begins to drop as the pressure across the screen 52 and pad 53 are reduced. A sharp drop in voltage can be seen at 102 in FIG. 7B as the pad 53 is expelled from the screen 52 at the beginning of the next expulsion stroke 94.

When the apparatus 10 is turned on, the electrodes 58, 59 may initially produce erratic and inconsistent measurements until the electrodes 58, 59 have stabilized. This phenomenon is schematically represented in FIG. 7B where the measured voltage produced during the second cycle between the 2 and 4 second time interval is noticeably smoother than the voltage measured during the first cycle. To achieve equilibrium of the electrodes 58, 59, motor 62 is run continuously during the initial measurement period for about 15 to 30 seconds until the voltage measurements indicate that the electrodes 58, 59 have reached a stable equilibrium.

The instantaneous position of motor 62 is determined for at least one point during each cycle of the bellows 60. The position information may be used to ascertain the sign of the electrode outputs relating to streaming potential. Instantaneous position of the bellows 60 may be determined by use of a proximity sensor 61, such as a conductivity sensor, an optical sensor, a capacitance sensor, or the like. Proximity sensor 61 senses the position of the bellows 60 by measuring the position of the crank arm 67. For example, an optical proximity sensor 67 may employ the use of a reflective tab which is attached to the crank arm 67. Each time the crank arm moves the reflective tab into a beam of laser light being emitted by the proximity sensor 67, laser light is reflected off the tab toward a photodetector in the sensor 67. When the photodetector senses light having wavelength(s) and intensity characteristic of laser light being reflected from the tab, the sensor 67 determines that it has detected the presence of the tab and outputs a signal to the PLC 50. In a preferred embodiment, the proximity sensor uses magnetism to sense the presence of a single metal rod section cut from an Allen wrench and inserted into a rotating part of the motor assembly 62. The output of the proximity sensor 61 is used by the PLC 50 to enable it to compare streaming potential measured (a) during the suction stroke (96 in FIG. 7A) when the fiber pad 53 is forming on the screen 52 and streaming potential is building to a peak, and (b) near the end of the expulsion stroke (94 in FIG. 7A) when there is no significant pressure across the screen 52 and streaming potential is at its lowest value.

Addition of 100 milli-equivalents of Bufloc™ 536 polydiallyldimethylammonium chloride (DADMAC) cationic additive eliminated the oscillatory effect of the electrical signal shown in FIG. 7B. In other words, there was no observed systematic difference in measured potential as the bellows was moved. Addition of further cationic polymer solution caused the re-emergence of a differential or oscillatory signal 90, responding to the position of the bellows.

However, this time the phase of the signal was reversed. In other words, the lowest value of the signal 90 was observed when the bellows was in its most contracted position. Subsequent tests with a conventional streaming potential apparatus confirmed that the initially anionic de-inked pulp furnish had been converted to a net positive charge by means of the added DADMAC solution. The maximum signal, when comparing the peak (with fiber pad present) to the baseline, had an absolute value of about 2 mV. These test results show, in principle, that the invention is capable of sensing the sign of streaming potential very rapidly and conveniently. It follows that it can be used for titration endpoint detection during automated determination of colloidal charge.

As a further check on the basic operation of the device, the same cationic furnish was further treated with sodium sulfate in order to increase the electrical conductivity to about 4 mS/cm. Consistent with the theory of streaming potential, the peak-minus-baseline signal was decreased to less than 0.2 mV. However, the sign of the signal, comparing peak to baseline, was unchanged.

EXAMPLE 2

Additional measurements were carried out using the apparatus described in Example 1 above with each measurement employing a different size screen. A fresh sample of the same de-inked pulp was diluted with distilled water to a consistency of about 0.4% as before. Results were as follows:

| Diameter Of Exposed Screen | Area Of Screen | Peak-minus-baseline Signal Magnitude |
| --- | --- | --- |
| 0.75 inches | 0.442 in$^2$ | 1.5 mV |
| 0.50 inches | 0.196 in$^2$ | 6.0 mV |
| 0.312 inches | 0.077 in$^2$ | 8.0 mV |

These results are consistent with the higher rate of flow, thicker pad, and greater differential pressure across a fiber pad of smaller area. As predicted by the Helmholtz-Smoluchowsi equation, the higher applied pressure differences resulted in a greater signal.

EXAMPLE 3

Figure 8:
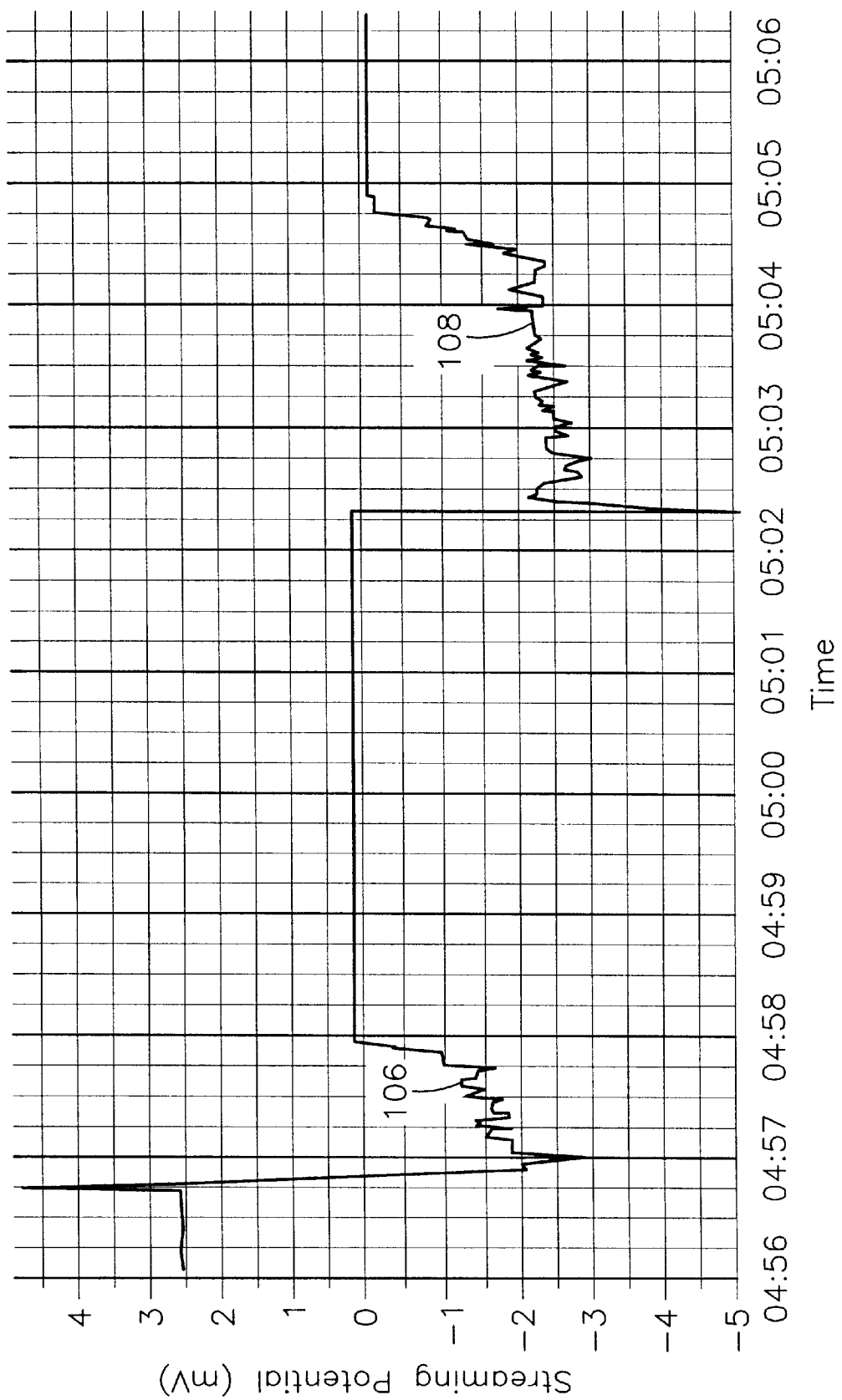
FIG. 8 is a graphical illustration of two streaming potential test measurements showing how streaming potential of a fiber solution varied over time as the fiber solution was titrated to zero or near zero streaming potential.

The apparatus described in Example 1 was next evaluated with a modified design of the first section 22 having an internal diameter of 3 inches, a wall thickness of 0.25 inches, and a fill level calibrated to contain 500 ml of slurry sample 24. The position of the screen 52 and adjoining part of the second section 54 was offset from the center of the base of the first section 22. The screen 52 was a standard woven stainless steel screen of mesh size 100 having an opening of approximately 140 μm. The experiment was performed in a fully automatic mode, except that, as an option, the sample chamber 22 was filled manually. In other respects, the apparatus was the same as in Example 1. The results of two different measurements are shown in FIG. 8. The titration curve 106 on the left side of the graph shows that as the sample was titrated with poly-diallyldimethylammonium chloride (Bufloc 536), streaming potential steadily increased toward zero potential, at which point no additional titrant was added.

An excess concentration of about 8,000 ppm of acrylamide-acrylate copolymer (Calgon 48B) was then added to a replicate sample of furnish in order to perturb the colloidal charge of the furnish in a way that is representative of effects of process variations encountered during a typical papermaking operation. The new furnish was titrated in like manner to a zero potential endpoint and the titration curve 108 on the right side of FIG. 8 was produced.

An interesting observation which can be gleaned from titration curve 108 is that the streaming potential did not begin to change until very late in the titration process. Even though the titrant pump started operating about 50 seconds after the start of the test, the streaming potential signal remained almost horizontal for approximately 90 seconds. This observation is consistent with a preferential reaction in the solution between excess anionic copolymer and the titrant. Only after the excess anionic material was exhausted did the cationic titrant begin to affect the potential at the fiber surfaces.

It is contemplated, and will be apparent to those skilled in the art from the foregoing specification, drawings, and examples that modifications and/or changes may be made in the embodiments of the invention. Accordingly, it is expressly intended that the foregoing are only illustrative of preferred embodiments and modes of operation, not limiting thereto, and that the true spirit and scope of the present invention be determined by reference to the appended claims.

What is claimed is:

1. An apparatus for determining an electrical characteristic of a papermaking furnish containing a dispersion of fibers, the apparatus comprising:
   a sample chamber for containing a measured amount of a papermaking furnish sample containing dispersed fibers, said chamber having first and second sections;
   a screen separating the first and second sections of said sample chamber, said screen having a first side adjacent the first section of the sample chamber and a second side opposite the first side and adjacent the second section of the sample chamber;
   means for urging at least a portion of the furnish sample through said screen in alternating directions between the first and second sections of the chamber so that furnish flows back and forth through said screen in a plurality of cycles, wherein during each cycle furnish is moved through the screen in a first direction during a first period of time from the first section of the chamber to the second section of the chamber to form a pad of fibers adjacent the first side of the screen and furnish is moved through the screen in a second direction during a second period of time from the second section of the chamber to the first section of the chamber to push the pad of fibers from the screen to be redispersed in the furnish sample in the first section of the chamber, wherein the total time consumed in moving the furnish through the screen during the first and second periods of time equals one cycle period;
   a first electrode within the first section of the sample chamber for sensing an electrical characteristic of the papermaking furnish and producing a first electrode signal corresponding to the electrical characteristic sensed;
   a second electrode within the second section of the sample chamber for sensing an electrical characteristic of the papermaking furnish and producing a second electrode signal corresponding to the electrical characteristic sensed; and
   a voltmeter electrically connected to said electrodes to receive and process the first and second electrode signals, producing a voltmeter signal that corresponds to the potential difference between the electrodes at one or more points in time during each cycle period.

2. The apparatus of claim 1 wherein said means for urging includes:
   a variable volume chamber in fluid communication with the second section of the sample chamber, said variable volume chamber having a moveable element which is moveable between a high volume state corresponding to the end of the first period of each cycle and a low volume state corresponding to the end of the second period of each cycle;
   wherein during transition of the moveable element between the low volume and high volume states, fluid is urged through the screen from the first section of the chamber to the second section of the chamber causing the pad of fibers to build up on the first side of the screen, and during transition of the moveable element between the high and low volume states, fluid is urged through the screen from the second section of the chamber to the first section of the chamber causing the pad of fibers to be pushed off the screen into the first section of the chamber; and
   a motor connected to move said movable element between said high and low volume states so that fluid moves in said first direction when the movable element is moved to the high volume state and fluid moves in said second direction when the movable element is moved to the low volume state.

3. The apparatus of claim 2 wherein said moveable element includes a bellows.

4. The apparatus of claim 2 wherein said moveable element includes a piston, said apparatus further comprising;
   an elongate cylinder in flow communication with the second section of the chamber and sealably housing said piston; and
   a linkage interconnecting the piston and motor so that the piston is driven along a reciprocal path within the cylinder between the high and low volume states during operation of the motor;
   wherein as the piston transitions between the low volume and high volume states, fluid is urged through the screen from the first section of the chamber to the second section of the chamber to build the pad of fibers on the first side of the screen, and the pad of fibers is pushed off the screen into the first section of the chamber by fluid which is urged through the screen from the second section of the chamber to the first section of the chamber during transition of the piston between the high and low volume states.

5. The apparatus of claim 1 wherein said means for urging includes:
an elongate conduit being a portion of the second section of the sample chamber;
a moveable support member connected to sealably support said screen within the elongate conduit;
a barrier positioned intermediate said screen and a portion of said elongate conduit to inhibit movement of fluid between the first and second sections of the chamber except through the screen; and
a motor for driving said support member along a reciprocal path so that said screen reciprocates between axially spaced-apart first and second positions;
wherein a pad of fibers is formed on the first side of the screen as the screen moves from the second position to the first position and fluid flows through the screen, and the pad of fibers is displaced from the first side of the screen as the screen moves from the first position to the second position.

6. The apparatus of claim 1 wherein said cycle period is about two seconds.

7. The apparatus of claim 1, further comprising means for mixing furnish in the first section of the sample chamber to assist in the release and redispersion of the fiber pad from the screen and into the furnish sample.

8. The apparatus of claim 1 wherein said screen includes a woven fabric of plastic or stainless steel strands or a perforated sheet of stainless steel having openings in the size range of 0.02 to 0.5 mm diameter.

9. The apparatus of claim 1 wherein said first and second electrodes are fabricated from a silver alloy.

10. The apparatus of claim 1, further comprising a water spray mechanism for rinsing and cleaning said sample chamber and screen after the plurality of measurement cycles is completed.

11. The apparatus of claim 1, further comprising a programmable controller for automatically controlling the operation of the apparatus, including said means for urging.

12. An apparatus for determining an electrical characteristic of a papermaking furnish, the apparatus comprising:
a sample chamber for containing a measured amount of a papermaking furnish sample containing dispersed fibers, said chamber having first and second sections;
a variable volume chamber in fluid communication with the second section of the sample chamber, and bounded at least in part by a movable element which is movable in cycles between a first limit position corresponding to a high volume state and a second limit position corresponding to a low volume state, wherein the time consumed during movement of the movable element from the first limit position to the second limit position and back to the first limit position comprises one cycle period;
a screen separating the first and second sections of said sample chamber, said screen having a first side adjacent the first section of the sample chamber and a second side opposite the first side and adjacent the second section of the sample chamber;
means for urging at least a portion of the furnish sample through said screen in alternating directions between the first and second sections of the chamber so that furnish flows back and forth through said screen in a plurality of cycles, wherein during each cycle furnish is moved through the screen in a first direction during a first portion of the cycle period from the first section of the chamber to the second section of the chamber to form a pad of fibers adjacent the first side of the screen and furnish is moved through the screen in a second direction during a second portion of the cycle period from the second section of the chamber to the first section of the chamber to push the pad of fibers from the screen to be redispersed in the furnish sample in the first section of the chamber;
a first electrode within the first section for sensing an electrical characteristic of the papermaking furnish and producing a first electrode signal corresponding to the electrical characteristic sensed;
a second electrode within the second section for sensing an electrical characteristic of the papermaking furnish and producing a second electrode signal corresponding to the electrical characteristic sensed; and
a voltmeter electrically connected to said electrodes to receive and process the first and second electrode signals, producing a voltmeter signal that corresponds to the potential difference between the electrodes at one or more points during each cycle period.

13. The apparatus of claim 12 wherein the movable element of said variable volume chamber includes a bellows.

14. The apparatus of claim 12 wherein the movable element of said variable volume chamber includes a piston, said apparatus further comprising:
an elongate cylinder in flow communication with the second section of the chamber and sealably housing said piston; and
a linkage interconnecting the piston and motor so that the piston is driven along a reciprocal path within the cylinder between the high and low volume states during operation of the motor;
wherein as the piston transitions between the low volume and high volume states, fluid is urged through the screen from the first section of the chamber to the second section of the chamber to build the pad of fibers on the first side of the screen, and the pad of fibers is pushed off the screen into the first section of the chamber by fluid which is urged through the screen from the second section of the chamber to the first section of the chamber during transition of the piston between the high and low volume states.

15. The apparatus of claim 12 wherein said screen includes a woven fabric of plastic or stainless steel strands or a perforated sheet of stainless steel having openings in the size range of 0.02 to 0.5 mm diameter.

16. The apparatus of claim 12 wherein said first and second electrodes are comprised of a silver alloy.

17. The apparatus of claim 12 wherein said means for urging includes a motor connected to said movable element.

18. The apparatus of claim 12 wherein each cycle period is about two seconds.

19. The apparatus of claim 12, further comprising a water spray mechanism for dispensing water to rinse and clean said sample chamber and said screen.

20. The apparatus of claim 12, further comprising:
a source of papermaking furnish;
a furnish supply conduit in flow communication with said sample chamber and said source of papermaking furnish for conducting the furnish sample from the furnish source to the sample chamber; and a metering device for metering a known amount of furnish from the furnish supply into the sample chamber to produce the furnish sample.

21. The apparatus of claim 12, further comprising:

a source of charged additive;

a flow conduit in flow communication with said source of charged additive;

a metering device for metering a measured amount of the charged additive into the sample chamber; and means for mixing the charged additive with the furnish sample.

22. The apparatus of claim 12, further comprising a programmable controller for controlling the operation of the apparatus including movement of said movable element.

23. A method for determining an electrical characteristic of a papermaking furnish containing a dispersion of fibers, said method comprising the steps of:

providing a furnish sample comprised of a measured amount of papermaking furnish in a container having first and second sections;

separating the first and second sections of the container with a fiber-collecting screen having a first side adjacent the first section of the container and a second side opposite the first side and adjacent the second section of the container;

reciprocally urging at least a portion of the furnish sample back and forth from the first side of the fiber-collecting screen to the second side of the screen between the first and second sections of the container during a plurality of cycles;

wherein during a first portion of each cycle fibers from the furnish sample build up to form a pad on the first side of the screen as furnish flows in a first direction from the first to the second section of the container, and during a second portion of each cycle the pad is pushed off the first side of the screen and the fibers thereof redispersed into the furnish in the first section of the container as fluid flow is reversed causing fluid to move in a second direction from the second to the first section of the container, thus producing and expelling at least a single fiber pad during each cycle;

wherein each cycle includes a single movement of furnish through the screen in the first direction and a single movement of furnish through the screen in the second direction and the time consumed to complete one cycle is a cycle period; and measuring an electrical characteristic of the furnish sample across each fiber pad at least once during each cycle period.

24. The method of claim 23 wherein said cycle period is about two seconds.

25. The method of claim 23 wherein said step of reciprocally urging further includes the steps of:

providing a variable volume chamber in fluid communication with the second section of the container and having a movable element which is movable between a first position corresponding to a high volume state and a second position corresponding to a low volume state;

wherein during transition of the moveable element between the low volume and high volume states, fluid is urged through the screen from the first section of the chamber to the second section of the chamber causing the pad of fibers to build up on the first side of the screen, and during transition of the moveable element between the high and low volume states, fluid is urged through the screen from the second section of the chamber to the first section of the chamber causing the pad of fibers to be pushed off the screen into the first section of the chamber; and moving said movable element between said first and second positions so that fluid moves through the screen in the first direction when the movable element is moved to the first position and fluid moves through the screen in the second direction when the movable element is moved to the second position.

26. The method of claim 23 wherein said moving step further includes the steps of:

attaching a moveable support member to the screen;

limiting the flow of furnish around the screen; and moving the support member along a reciprocal path so that said screen moves back and forth within the furnish sample to produce movement of furnish through the screen in said first and second directions.

27. An apparatus for determining an electrical characteristic of a papermaking furnish containing a dispersion of fibers, the apparatus comprising:

a sample chamber for containing a measured amount of a papermaking furnish sample containing dispersed fibers, said chamber having first and second sections;

a screen separating the first and second sections of said sample chamber, said screen having a first side adjacent the first section of the sample chamber and a second side opposite the first side and adjacent the second section of the sample chamber;

means for urging at least a portion of the furnish sample through said screen in alternating directions between the first and second sections of the chamber so that furnish flows back and forth through said screen in a plurality of cycles, wherein during each cycle furnish is moved through the screen in a first direction during a first period of time from the first section of the chamber to the second section of the chamber to form a pad of fibers adjacent the first side of the screen and furnish is moved through the screen in a second direction during a second period of time from the second section of the chamber to the first section of the chamber to push the pad of fibers from the screen to be redispersed in the furnish sample in the first section of the chamber, wherein the total time consumed in moving the furnish through the screen during the first and second periods of time equals one cycle period;

first and second electrodes within the sample chamber for sensing an electrical characteristic of the papermaking furnish and producing first and second electrode signals corresponding to the electrical characteristic sensed; and a voltmeter electrically connected to said electrodes to receive and process the first and second electrode signals, producing a voltmeter signal that corresponds to the potential difference between the electrodes at one or more points in time during each cycle period.

28. The apparatus of claim 27 wherein said first electrode is positioned within the first section of the sample chamber and said second electrode is positioned within the second section of the sample chamber.

29. The apparatus of claim 27 wherein said means for urging includes:

a variable volume chamber in fluid communication with the second section of the sample chamber, said variable volume chamber having a moveable element which is moveable between a high volume state corresponding to the end of the first period of each cycle and a low volume state corresponding to the end of the second period of each cycle;

wherein during transition of the moveable element between the low volume and high volume states, fluid is urged through the screen in a first direction from the first section of the chamber to the second section of the chamber causing the pad of fibers to build up on the first side of the screen, and during transition of the moveable element between the high and low volume states, fluid is urged through the screen in a second direction from the second section of the chamber to the first section of the chamber causing the pad of fibers to be pushed off the screen into the first section of the chamber; and a motor operably connected to said movable element to move said movable element between said high and low volume states so that fluid moves in said first direction when the movable element is moved to the high volume state and fluid moves in said second direction when the movable element is moved to the low volume state.

* * * * *

UNITED STATES PATENT AND TRADEMARK OFFICE
CERTIFICATE OF CORRECTION

PATENT NO. : 5,936,151
DATED : August 10, 1999
INVENTOR(S) : Martin Allen Hubbe

It is certified that error appears in the above-identified patent and that said Letters Patent is hereby corrected as shown below:

Column 5, line 30 after "plurality of" delete --a--.

Column 14, line 12, after "49" delete "to be used for" and insert therefore --to use for--.

Column 14, line 27 after "embodiment" add a comma --,--.

Signed and Sealed this

Thirteenth Day of June, 2000

Attest:

Q. TODD DICKINSON

*Attesting Officer*        *Director of Patents and Trademarks*